(12) United States Patent
Saischek et al.

(10) Patent No.: US 6,229,008 B1
(45) Date of Patent: May 8, 2001

(54) α-D-PENTOFURANOSIDES, AND A PROCESS FOR PREPARING THE SAME

(76) Inventors: Jörn Saischek, Burgasse 8/1/6, Graz (AT), A-8010; Berndt Stadelmann, #54C, 4, III, West City CT., TX (US) 79902

( * ) Notice: Subject to any disclaimer, the term of this patent is extended or adjusted under 35 U.S.C. 154(b) by 0 days.

(21) Appl. No.: 08/793,515
(22) PCT Filed: Aug. 25, 1995
(86) PCT No.: PCT/AT95/00169
  § 371 Date: Apr. 18, 1997
  § 102(e) Date: Apr. 18, 1997
(87) PCT Pub. No.: WO96/06103
  PCT Pub. Date: Feb. 29, 1996

(30) Foreign Application Priority Data

Aug. 25, 1994 (AT) .................................................... 1642/94

(51) Int. Cl.[7] .............................. C07H 11/00; C07H 1/00
(52) U.S. Cl. .......................... 536/118; 536/122; 536/124
(58) Field of Search .................................... 536/118, 122, 536/124

(56) References Cited

U.S. PATENT DOCUMENTS 5,336,764 * 8/1994 Marquez et al. ....................... 536/4.1
5,459,256 * 10/1995 Marquez et al. .................. 536/27.14

FOREIGN PATENT DOCUMENTS

0274511 * 9/1992 (CS) .
0 215 722 3/1987 (EP) .
9715585 * 5/1979 (WO) .
92 01700 2/1992 (WO) .
9221343 * 12/1992 (WO) .
9606103 * 2/1996 (WO) .
9606851 3/1996 (WO) .

OTHER PUBLICATIONS

Wysocki et al., "A More Expedient Approach to the Synthesis of Anti–HIV–Active 2.3–Dideoxy–2–fluoro–β–D–threo–pentofuranosyl Nucleosides," *Synthesis*, 1005–1008 (Nov. 1991).

Howell et al., "Antiviral Nucleosides. A Stereospecific, Total Synthesis of 2'–Fluoro–2'–doexy–β–D–arabinofuranosyl Nucleosides," *J. Organic Chemistry*, 53(1), 85–88 (Jan. 8, 1988).

Hiebl et al., "Synthase von Glycofuranosylformamiden, –isocyaniden und –isocyanaten Ausghend von den Entsprechen den Glycosylaziden," *Liebegs Annalen der Chemie*, (Issue No. 8), 765–774 (Aug. 1988).

Ceulemans et al., "Synthesis of 3'–Fluoro–3'–deoxy–N[6]–cyclopentyladenosine," *Nucleosides & Nucleotides*, 13(9), 1991–2000 (Sep. 1994).

Fleischner et al., "New Compounds: Synthesis of D–Arabinofuranosylurea Derivatives," *J. Pharmaceutical Sciences*, 66(8), 1206–1208 (Aug. 1988).

Haradahira et al., "Synthesis and Biodistribution of a Fluorine–18 Labeled Analogue of D–Talose: 2–Deoxy–2–[$^{18}$F] fluoro–D–talose," *Applied Radiation and Isotopes*, 43(5), 627–632 (1992).

Yoshimura et al., "A Novel Synthesis of New Antineoplastic 2'–Deoxy–2'–Substituted–4'–thiocytidines," *J. Organic Chem.*, 61(3), 822–823 (Feb. 9, 1996).

Liptak et al., "Hydrogenolysis of 3, 5–O–Benzylidene Acetals with the $LiAlH_4$–$AcCl_3$ Reagent in Methyl D–Xylofuranosides," *Tetrahedron*, 37(13), 2379–2382 (1981).

Nicotra et al., "Chemoenzymatic Approach to Carbohydrate–Derived Analogues of Platelet–Activating Factor," *J. Organic Chem.*, 57(7), 2154–2158 (Mar. 27, 1982).

Maryanoff et al., "Synthesis of C–Arabinofuranosyl Compounds. Phosphonate and Carboxylate Isosteres of D–Arabinose 1,5–Bis–Phosphate," *Carbohydrate Research*, 171, 259–278 (Dec. 31, 1987).

Chretien et al., "ATDP Salts; 22. A Novel and Efficient Method for the Preparation of Glycosyl Azides via Alkoxy–Tris [dimethylamino]–phosphonium Salts," *Synthesis*, (Issue No. 12), 937–939 (Dec. 1979).

Fulcrand–El Kattan et al., "Synthesis and Biological Properties of 5–o–Carboranyl–1–(2–deoxy–2–fluoro–β–D–arabinofuranosyl)uracil," *J. Medicinal Chem.*, 37(16), 2583–2588 (August 5, 1994).

(List continued on next page.)

*Primary Examiner*—Cecilia Tsang
*Assistant Examiner*—L. Eric Crane
(74) *Attorney, Agent, or Firm*—Jacobson, Price, Holman & Stern, PLLC

(57) ABSTRACT

α-D-pentofuranoside derivatives have the general formula (D), in which R stands for $(C_1-C_4)$alkyl that is non-substituted or substituted one or several times by halogen, $(C_1-C_4)$alkyl, $(C_1-C_4)$alkoxy and/or phenyl, and $R_1$ stands for $[(C_6-C_{20})aryl]_k$-$[(C_1-C_4)alkyl$ or $[(C_6-C_{20})]aryl]_k$-$[(C_1-C_{12})alkyl]_{(3-k)}Si$ in which k=0 to 3, that are non-substituted or substituted one or several times by halogen, $(C_1-C_4)$alkyl, $(C_1-C_4)$alkoxy and/or $(C_6-C_{20})$ aryl, or preferably a benzyl that is non-substituted or substituted one or several times by the above substituents. Also disclosed are starting and intermediary compounds, up to furanosides (D) having an analogous structure, processes for preparing said furanosides and their precursors, and their use.

(D)

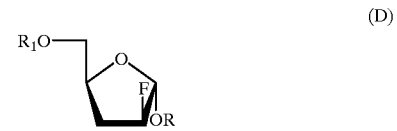

20 Claims, No Drawings

OTHER PUBLICATIONS

Marquez et al.(II), "Acid–Stable 2'–Fluoro Purine Dideoxynucleosides as Active Agents Against HIV," *J. Medicinal Chem.*, 33(3), 978–985 (Mar. 1990).

Chou et al., "Synthesis and Biological Effects of 2'–Fluoro–5–Ethyl–1–β–D–Arabinofuranosyluracil," *Antimicrobial Agents and Chemotherapy*, 31(9), 1355–1358 (Sep. 1987).

McClard et al., "Inhibition of Fructose Bisphosphate and Stimulation of Phosphofructokinase by a Stable Isosteric Phosphonate Analog of Fructose 2,6–Bisphosphate," *Archives of Biochemistry and Biophysics*, 245(1), 282–286 (Feb. 15, 1986).

Rao et al., "Removal of O–Benzyl Protecting–Groups of Carbohydrate Derivatives by Catalytic, Transfer Hydrogenation," *Carbohydrate Research*, 83(1), 175–177 (Aug. 1, 1980).

Su et al.(I), "Improved Synthesis of an α–D–Ribofuranoside via Stereoselective Alkylation of a Dibutylstannylene Derivative for Ready Access to the 2–Substituted 2–Deoxyarabinofuranosides," *J. Organic Chem.*, 47(8), 1506–1509 (Apr. 9, 1982).

Su et al. (II), "Facile Synthesis of 2–Deoxy–2–substituted–D–arabinofuranose Derivatives," *J. Organic Chem.*, 46(9), 1790–1792 (Apr. 24, 1981).

Lloyd et al., "Some Intramolecular Rearrangements When Pentofuranoses Are Treated with Diethylaminosulfur Trifluoride (DAST)," *J. Fluorine Chem.*, 60(2–3), 239–250 (Feb. 1993).

Yoshimura et al., "Preparation of 2'–Deoxy–2'–(Substituted or Unsubstituted methylidene)–4'–thionucleosides as Antitumor Agents," Abstract of W096–01834, Jan. 25, 1996; *Chem. Abstr.*, 124(23), pp. 1284–1285, Abstr. No. 317789w (Jun. 3, 1996); only Abstract supplied.

Tetrahedr. Lett., vol. 33, 1992, pp. 7511–7514, M.E. Maier Und T. Bradstetter, "Synthesis of an Oxabicyclo (7.2.1) Enediyne from a Furanoside Derivative", Dec., 1992.

J. Chem. Soc., 1946, pp. 100–101, R.J. McIlroy, "Trityl Derivatives of Xylofuranose", Part I.

Chem. Pharm. Bull., vol. 22, 1974, pp. 2318–2323, M. Taniguchi et al. "Stereochemical Studies. XXXI. Total Synthesis of Several D–Pentose Derivatives", Issue No. 10, Oct., 1974.

J. Carbohydr. Chem., vol. 4, 1985, pp. 333–345, H. Kuzuhara, K. Hatana "A General Method for Stepwise Elongation of the (1–)5)–alpha–D–Arabinofuran Chain", Issue No. 3.

Carbohydr. Res., vol. 67, 1978, pp. 349–356, F.M. Unger et al. "Synthesis of 5,6,–Dideoxy–6–Phosphono–D–arabino–Hexose" Dec., 1978.

J. Org. Chem., vol. 26, 1961, pp. 4609–4612, D.V. Myhre Und F. Smith, "Synthesis of Xylobiose", Nov., 1961.

J. Am. Chem. Soc., vol. 80, 1958, pp. 4683–4692, R.E. Schaub Und M.J. Weiss, "The Synthesis of the Four Possible Methyl 3–Amino–3–Deoxy–D–Xylosides", Sep. 5, 1958.

Chem. Ber., 1942, pp. 1127–1140, K. Zeile Und W. Kruckenberg, "Über Phosphorylierungs– und Tritylierungsreaktionen", V. 75(10),Oct. 7, 194.

Chem. Zvesti, vol. 25, 1971, pp. 460–466, P. Kovac, "Alternative Synthesis of Methylated Sugars", Issue No. 6.

Agric. Biol. Chem., vol. 28, 1964, pp. 900–907, H. Kuzuhara Und S. Emoto, "Studies on the D–Xylose Series Part III", Issue # 12.

J. Org. Chem., vol. 50, 1985, pp. 3644–3647, C.H. Tann et al. "Fluorocarbohydrates in Synthesis", Issue No. 19.

Nucleosides & Nucleotides, vol. 7, 1988, pp. 155–165, J. Prisbe et al., "Synthesis and Anti–Herpetic Activity of a 2'–Fluoro–arabinosyl Analog of Trifluridine", Issue No. 2.

Carbohydr. Res., vol. 108, 1982, pp. 97–101, P.J. Garegg et al., "A Novel, Reductive Ring–Opening of Carbohydrate Benzylidene Acetals".

Tetrahedr., vol. 37, 1981, pp. 2379–2382, A. Liptak et al., "Hydro–genolysis of 3,5–0–Benzylidene Acetals with the LiA1H4–A1C13 Reagent in Methyul D–Oxylfuranosides", Issue # 13.

Chem. Ind., 1970, pp. 94–95, J. Hildesheim et al., "An Elimination Reaction with Sodium Benzoate–Dimethylformamide, Leading to a Furanoid–Vinyl–Tosylate", Issue No. 3, Jan. 17, 1970.

\* cited by examiner

α-D-PENTOFURANOSIDES, AND A PROCESS FOR PREPARING THE SAME

The anti-viral and anti-carcinogenic action of many nucleosides, which are used as pharmaceutical products, is of extremely great interest in medical circles. In recent years, fluorine-containing nucleosides in particular have become increasingly important. Compared with hydroxyl groups, fluorine atoms bond strongly to carbon atoms; they are for the most part chemically inert and have hydrophobic properties. On the other hand, the size of their atoms is similar to the size of hydroxyl groups. If, therefore, hydroxyl groups of a nucleoside are substituted by fluorine atoms, one can expect to obtain an excellent metabolic-antagonistic effect.

Many fluorine-containing nucleosides have already been studied to determine their anti-viral properties and their cytotoxicity. The unusual properties of pyrimidine nucleosides having the formula (T0) defined later herein, and of purine derivatives having the formula (U0), suggest that these substances can be used as therapeutic agents to treat viral, and in particular retroviral infections, such as AIDS, etc.

It is, however, a difficult matter to prepare these target substances. Conventional methods of preparation on a laboratory scale are technically complex, operate with toxic chemicals, and provide low overall yields, which in particular for reasons of costs cannot be improved upon.

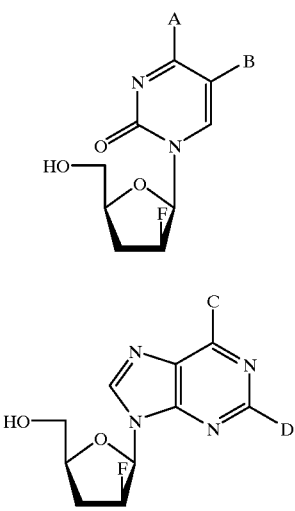

(T0)

(U0)

A . . . OH, NH$_2$, OR', NR'$_2$ R' in A,
B, C, D denotes the usual substituents
B . . . H, CH$_2$, CH=CHBr, halogen
C . . . H, NH$_2$, Cl, OR', S', NHR', NR'$_2$, OX$^+$
D . . . H, halogen, NH$_2$, NR'$_2$, N$_3$ In principle, two modifications must be carried out on the carbohydrate part of the nucleoside: the deoxygenation of the 3-position, as well as the introduction of fluorine into the 2-position.

To perform these modifications of the functionality on the natural nucleoside is a difficult and protracted procedure. For example, Shiragami et al., J. Carbohydrates, Nucleosides & Nucleotides, 11 (2–4), 391–400 (1982) at first produce cordycepin by regioselective bromination, followed by hydrogenolysis, and the cordycepin is then converted by fluorination with diethylaminosulphur trifluoride (DAST fluorination), with a low yield, into 9-(2,3-dideoxy-2-fluoro-β-D-threo-pentofuranosyl-adenine (2-Fdda). Therefore, in most of the synthesis strategies used so far, first the fluorinated nucleoside was prepared, starting from 2-deoxy-2-fluoro-arabinofuranose derivatives and then the 3-position was deoxygenated. However, the Barton deoxygenation process used, or modifications thereof, cannot be considered as a sensible production strategy for the reasons just given (Marquez et al., J.Med.Chem., (1990), 33, 978–985; Vemishetti et al., EP 428.109; Barchi et al., J.Med.Chem., (1991), 34, 1647–1655; Machin et al., EP 292.023).

It therefore appeared advisable to carry out both manipulations of the carbohydrate part before the nucleoside synthesis.

In EP 463.470, Okabe et al. accordingly propose a complicated, low-yield, 11-stage synthesis of 2,3-dideoxy-2-fluoro-5-0-trityl-α-D-threopentofuranosyl chloride, see formula (C), as the precursor stage of the nucleoside.

An intermediate stage used in this process is obtained by Siddiqui et al., Tetr. Lett. (1994), 35, 3263–3266 from diacetone mannitol.

The hitherto most interesting method of preparing the modified carbohydrate part appears in WO 92/01700. Here, 2 Fdda is produced in a 9-stage synthesis starting from 1,3,5, tri-O-benzoyl-2-deoxy-2-fluoro-α-D-arabinofuranose. However, for synthesizing the decisive intermediate product, 5-O-benzoyl-2,3-dideoxy-2-fluoro-α-D-threopentofuranosyl bromide (see formula (Z)), it is also necessary to use the Barton deoxygenation method.

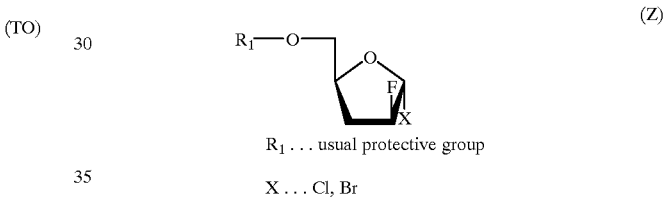

(Z)

R$_1$ . . . usual protective group

X . . . Cl, Br

A new, efficient way has been found of producing a similar but, when used, superior intermediate product:

In particular, the present invention relates to an astonishingly short and efficient method of synthesizing an α-furanoside having the general formula (D), described in detail later herein, in which the 5-position is protected by an ethereal protective group. This furanoside can easily be converted into a halogenose having the general formula (Z), which is dealt with in detail later herein, in which the 5-position is protected by an ethereal protective group.

Among other things, the subject of the invention is the important compound (D1) according to claim 2, which is also defined further below. It should be mentioned here that two, at first sight similar, compounds—methyl-5-0-benzoyl-2,3-dideoxy-2-fluoro-α-D-threopentofuranoside and methyl-5-0-(tertbutyl-diphenylsilyl)-2,3-dideoxy-2-fluoro-β-D-threopentofuranoside—were synthesized according to WO 92/01700 as the starting material for a halogenose having the general formula (Z); the compounds (D0), which will also be defined in more detail below, and in particular the important compounds (D1), are far superior to the aforementioned compounds, not only because of their stability in the course of the subsequent reactions, but also because of their better handling characteristics in the necessary purification operations (through suitable substitution, it is possible in each case to emphasize specifically desired properties). While the first-mentioned compound known from WO 92/01700 differs entirely from the new compounds (D0) and (D1) because of its own protective group, which is not of the ether but of the ester type, the second of the above-mentioned compounds also possesses a serious disadvantage because of its β-position of the aglycone and because of the protective group, which contains in particular ($D_1$) and leading to various valuable pharmaceutical active substances.

Diagram 1:

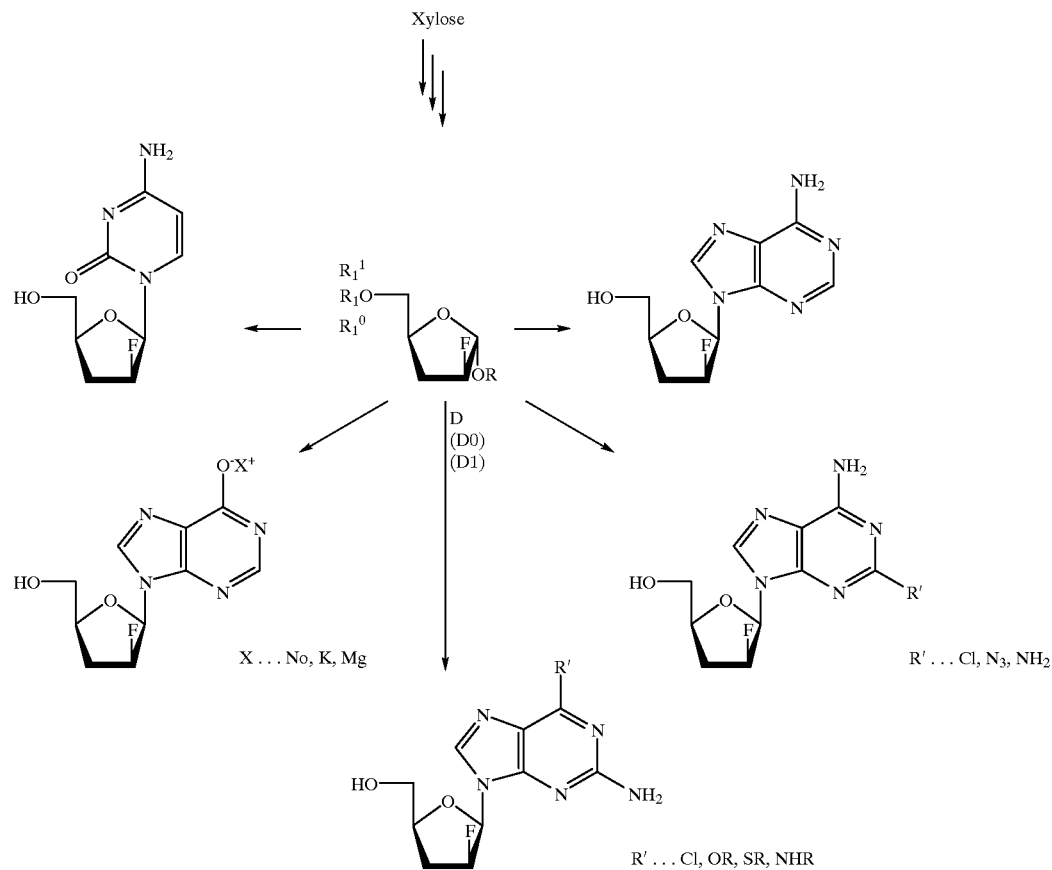

Si; protective groups of the type $R^0_1$, $R^1_1$, according to claims 1, 2 of this invention are significantly superior to the silicon protective groups as regards stability in the subsequent reactions.

These new, important compounds having the general formula (D) are obtained in the present invention by fluorination from alkyl-5-0-$R_1$-3-deoxy-α-D-xylofuranoside (a compound described later on and having the general formula (E)). According to Su et al. (JOC, (1981), 46, 1790–1792) fluorination of the corresponding β-material did not appear to be promising.

Methyl-5-0-benzoyl-3-deoxy-α-D-xylofuranoside (Jones et al., Tetr.Lett. (1991), 32, 247–250; Nair et al., JACS (1992), 114, 7951–7953) and methyl-3-deoxy-3-deutero-5-0-(4-methoxytrityl)-α-D-xylofuranoside (Pathak et al., Tetr..Lett. (1986), 42-5427–5441) have already been described as by-products in each case.

The present invention relates to a group of closely related pentofuranoside derivates which can easily be converted into each other, and which are important intermediate stages along the path to synthesizing the key compound referred to above; the invention also describes in detail advantageous methods of producing the said compounds and also the use of these compounds.

The following general diagram 1 provides an overview— by no means complete—of the possible range of conversions, starting from the key compound (D) or ($D_0$) or The following compounds are the subjects of the invention and together they form a unified group.

In detail, these compounds are the compounds (D0) according to claim 1.

Within the framework of the invention, compound (D1) according to claim 2 is in particular preferred. This is an important, central starting product for the uncomplicated, direct conversion into the protected nucleosides having the formula T and U. The essential advantage of these compounds (D1) is that, as was discovered, following suitable substitution of the ethereal protective group at the 5-position, it is possible to achieve high stability of the protective group, which is advantageous to the process, and much easier cleavage of the protective group; also, because the physical properties are modified by the substitution, by-products can be separated out in a technically advantageous manner in the individual stages of the process.

Compound (F) according to claim 3 is another subject of the invention. This compound is a starting product which can be easily converted for the purpose of ultimately obtaining compound (D) or (D0) or (D1) and (Z).

Another subject of the invention is compound (H) according to claim 4. This compound is an immediate starting compound for compound (F).

Furthermore, in particular the two stereoisomeric compounds (I) and (J) according to claim 5 are also subjects of the invention. They form the essential base compounds for a sequence of process steps, which in all cases contains a relatively small number of stages, with in each case high yields, which ultimately lead to the compounds having the formulae (D) or (D0) or (D1)) and (Z). As a precaution, it should be mentioned here that $(C_6-C_{20})$aryl denotes, for example, phenyl, naphthyl, 2-phenantryl or 2-triphenylenyl.

The above-mentioned subjects of the invention are members of a group of important new intermediate compounds used in the preparation of the above-mentioned pharmaceutical active substances which are needed, to a rapidly increasing extent, for the effective control of virus-induced diseases and cancer.

A further essential object of the invention is a new, uncomplicated and high-yield process for producing compounds of the type described, for example, in claim 6.

A further advantageous process method is based on the new compound (F) and is described in claim 7.

The process described in claim 8 is essentially carried out in three stages and, starting from the new compound (H), it leads, also with good yields, to the above-mentioned compound (D)or (D0) or (D1) and finally (Z).

Claim 9 covers a preferred high-yield process, made up of several individual stages, for obtaining (D) with a sequence of reaction steps, starting from α-configured β-pentofuranosides which can be obtained without difficulty from pentoses.

The subject of claim 10 is a less complicated but, as was found, effective variant of the above-mentioned process according to claim 9.

Despite the fact that they comprise multiple stages, both these last-mentioned variants of the process are characterized by simple, uncomplicated process control and surprisingly high yields.

In order to clarify and illustrate the individual reactions and reaction stages of the processes according to the invention so far described, which are employed to obtain (D) as well as the selected compounds (D0) or (D1)) covered by the formula (D), according to claims 6 to 10, attention is drawn in particular to Diagram 2, which is presented later herein; this diagram illustrates in a clear manner the preparation relationships between the various compounds and intermediate compounds according to, or obtainable according to, the invention.

The new, selective multi-stage synthesis of the target compounds (D), and also (D0) or (D1)), according to the invention, proceeds from the last-mentioned multi-stage process, from compounds having the formulae (I) and/or (J). Under the basic conditions of the reaction, $OR_3$ is eliminated and a compound having the formula (H) is formed, whose enolic ester is saponified and the compound (G) is formed, which is rearranged into a compound having the formula (F). In order to avoid almost totally any condensations similar to the aldol type, it is especially favourable to make the hydride donor available right from the start; this donor stereoselectively reduces the 2-ulose (F), formed by saponification and rearrangement, to a compound having the formula (D) or (D0) or (D1)). Since the stereochemical information of the 2 and 3-positions is lost at the enolic ester stage, any α-configured pentofuranoside whose 5-OH group is appropriately protected, can be used as the starting material.

Especially preferred α-configured pentofuranosides having the general formula (I), in which R denotes methyl, $R_1$ denotes substituted benzyl and $R_2$ and $R_3$ denote mesyl, can be obtained without difficulty by mesylation of compounds having the general formula (K), in which R denotes methyl and $R_1$ denotes substituted benzyl. Several methods are known for producing the above-mentioned compound (K), but must be rejected by an industrial chemist. For example, as early as in 1981 methyl-5-0-benzyl-α-D-xylofuranoside (Kawana et al., Bull. Chem. Soc. Jpn., (1981), 54, 1492–1504) was synthesized in a 6-stage, low-yield process, with only a 30% yield being attained in the last stage. An interesting approach, namely opening the benzylidene ring of methyl-3-5-0-benzylidene-α-D-xylofuranoside (Liptak et al., Tetrahedron (1981) 37, 2379–2382), possesses some serious disadvantages. For example, the use of $LiALH_4$ makes it impossible for safety reasons to use this reaction on a large scale; in addition, quite considerable quantities of by-products, such as (3-0-benzyl ether) are formed, and separating these from the desired main product, 5-0-benzyl ether, causes very serious problems.

Surprisingly, opening this benzylidene ring using the reagent $NaCNBH_3$/HCl leads, regioselectively to high yields of the desired compound (K1). While it is true that $NaCNBH_3$/HCl has already been described as a ring-opening reagent (Johansson et al., JCS Perkin Trans 1, (1984), 2371–2374, Garegg et al., Carb. Res. (1982), 108, 97–101), it was only applied to pyranosides. A further aspect of the present invention relates to an extremely efficient process for producing compounds having the general formula (O) according to claim 19.

All hitherto known methods for synthesizing xylofuranoside have the problem that they produce pyranosides as by-products. This situation can be improved by using trifluoroacetic acid as the catalyst (Dhawan et al. Carb. Res. (1988), 183, 47–57), but this cannot be employed on an industrial scale because the large amount of catalyst used (given in vol. % of the solvent) would greatly complicate the processing and also generate high procurement and disposal costs.

Astonishingly, the use of iodine ($I_2$) as the catalyst in catalytic quantities gives rise to almost pure α/β mixtures of furanosides. For example, by reacting D-xylose in an alcohol, excellent yields can be obtained using catalytic amounts of $I_2$ at reflux temperature. This is all the more astonishing since at reflux temperature the traditional methods produce pyranosides—which are not wanted here—as the main products.

Fischer glycosidation (reaction of D-xylose with an alcohol) takes place preferably in the presence of iodine ($I_2$) as the catalyst. The catalyst is used in concentrations of 0.1 to 20 mol %, relative to the amount of sugar used. The reaction temperature may be between room temperature and—preferably—reflux temperature, and the reaction times are between 1 and 48 hours, depending on the reaction conditions.

The reaction with non-substituted or substituted benzaldehyde dimethyl acetals is carried out in a customary, recognized manner employed without any problems by organic chemists—namely reacetalization in the presence of an acid catalyst.

The opening reaction of the non-substituted or substituted benzylidene ring of the α-anomer also does not pose the experimenter with any problems, if the reaction conditions are exactly maintained. The benzylidene ring and $NaCNBH_3$ are presented in an inert solvent and a solution containing an inorganic acid or Lewis acid is slowly added drop by drop in a way that either maintains a constant pH value and/or prevents gas from developing. The reaction temperatures may lie between −50 and +50° C. Alcohols or ethers are used as the preferred inert solvents.

The subsequent introduction of sulfonic acid ester groups at the 2 and 3 positions occurs in the presence of at least an equimolar amount of base—relative to sulfonyl halide. Organic bases such as tertiary amines, e.g. pyridine, may be used as bases; they may also be used as solvents.

The deoxygenation step takes place preferably in a solvent or in mixtures thereof, when mixtures are used, preferably one of them may be inert and also practically hydrophobic under the reaction conditions used. The solvents or mixtures thereof should in any case partially dissolve the reagents and starting compounds used. The solvents are advantageously selected from the group of aqueous, water-miscible, alcoholic, polyol or ether-like solvents, such as in particular alcohols, polyols and ethers, e.g. methanol/toluene, or dioxane/water mixtures, methanol, isopropanol, 2,3-butanediol, THF and/or ethylene glycol.

The bases may be inorganic bases such as KOH, NaOH, $Na_2CO_3$ or organic bases, such as in particular Na-oxalate, tetrabutylammonium oxalate and tetrabutylammonium fluoride. Favourable reaction temperatures occur in the range from 10 to +150° C., preferably from 40 to 80° C.

Typical hydride sources such as, in particular, sodium borohydride, lithium aluminium hydride, tertrabutylammonium borohydride, hydrogen in the presence of a catalyst, sodium hydride and diisobutylaluminium hydride may be considered as hydride donors.

Diagram 2:

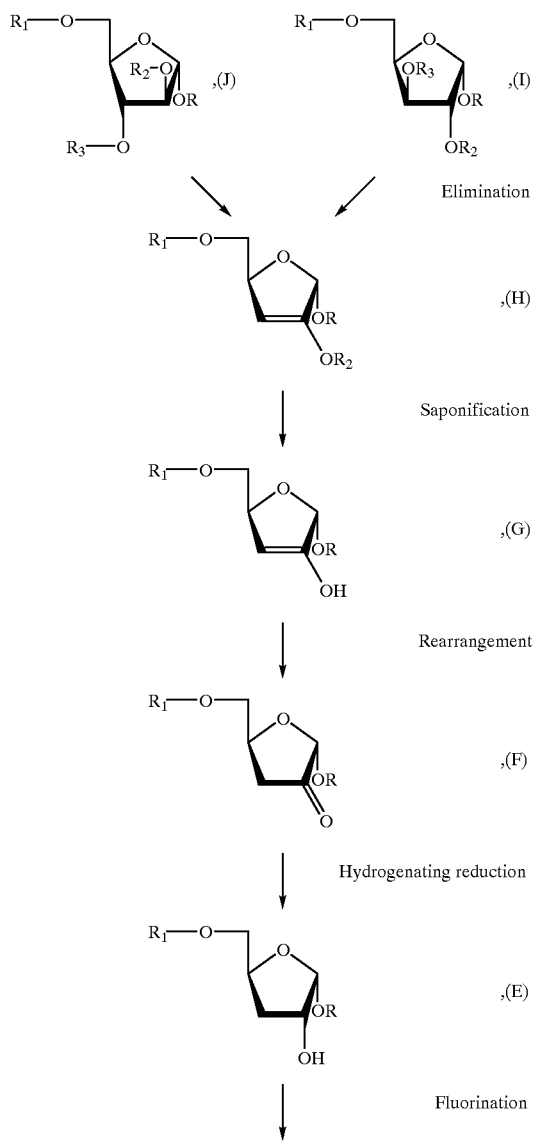

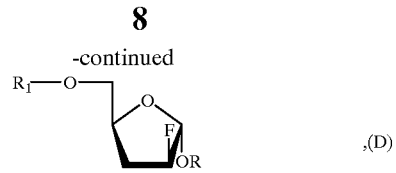

Elimination/deoxygenation reactions of a similar type to those found in the present invention (starting from (I) or (J) after (H) or (F) or (E)) are known, but they relate either to nucleosides (JOC, (1973), 38, 598-; (1973) 38, 1283-; J. Carbohydrates, Nucleosides, Nucleotides, (1975), 2, 47; Chem. Pharm. Bull., (1995) 23, 1411-), non-sugars (Tetr. Lett., 1980), 21, 2453) or sugars which possess neither the α-position of the aglycone required for the process, nor a suitable sugar configuration and also no inert protective group at the 5-position (Chem. Ind. (1970), 94, Carbohydrate Res. (1970), 14, 315).

The conversion of a compound having the formula (E) into a compound having the formula (D) according to the above diagram 2 may take place directly by reaction with DAST or through nucleophilic substitution of a suitable leaving group, such as the trifluoromethanesulfonyl group or the imidazolesulfonyl group. By way of example, the p-bromobenzenesulfonyl group should be mentioned as another suitable leaving group.

In order to introduce the leaving group, a compound having the formula (E) is presented in a solvent which is inert under the reaction conditions, e.g. chlorinated hydrocarbons, ethers, and at least an equimolar amount of base is added.

Organic bases such as pyridine, triethylamine and/or imidazole may be considered as the bases, and each base may be used alone as a diluent.

Next, a halide or anhydride of sulfonic acid or of carboxylic acid, such as trifluoromethanesulfonyl chloride or anhydride is added in an equimolar amount or in excess, while stirring. If the leaving group is the imidazolesulfonyl group, sulfuryl chloride is added in an equimolar amount or in slight excess, advantageously in the presence of an excess of imidazole. Purification may possibly be carried out through crystallization, column chromatographic separation or similar.

The fluorination is advantageously accomplished by adding at least an equimolar amount of a fluoride donor, such as potassium fluoride, sodium fluoride, cesium fluoride, tetraalkylammonium fluoride, in which methyl, ethyl, propyl and butyl groups are suitable as the alkyl groups, but the butyl groups are preferred, also polyhydrogen fluorides.e.g. pyridinium polyhydrogen fluoride, $KHF_2$, tetraalkylammonium bifluoride in a solvent which is inert under the selected reaction conditions, e.g. in particular chlorinated hydrocarbons, e.g. methylene chloride, ether, e.g. tetrahydrofuran, nitriles, e.g. acetonitrile, alcohols and polyols, e.g. butanol, ethylene glycol or mixtures of such solvents.

Depending on the way in which the reaction is controlled, the nucleophilic substitution of the leaving group by fluorine may also take place in the presence of an acid, such as HF or methanesulfonic acid. Depending on the method used, the reaction temperatures vary; however they lie within the range of −50 to +200° C.; under basic conditions −50 to +30° C. and under acid conditions 30 to 150° C. are preferred.

At this point it should especially be pointed out that the present invention is based in particular on the discovery that when ether protective groups are present in the 5 position in the compounds under discussion here, especially when compared to the hitherto normally used compounds possessing ester protective groups in that position, certain advantages, namely better stability in the preparation and subsequent reactions, easy and selective cleavage, also technically and economically advantageous processing possibilities, are obtained when preparing the various above-mentioned compounds, i.e. intermediate and target compounds, and also when further processing them into valuable active ingredients for pharmaceuticals.

A further subject of the invention is a preferred process, as outlined in claim 11, for further processing the target compound (D) into a compound (Z), which is an intermediate compound in the preparation of fluorine-containing nucleosides, which are important for the control of viral diseases and cancer, and also, but not necessarily, after condensation with a derivative of a nucleobase and subsequent cleavage of the protective group, pharmaceutically effective, final nucleosides from diagram 1 itself, especially for example the nucleosides (T) and (U) or (TO) and (UO) may be prepared.

Especially advantageous results may be obtained in the present case by employing the method described in claims 12 and 13.

Another important aspect is also the preparation of the various intermediates (E), (I), (H) accumulating or occurring at the end of the respective reaction stages in the process of obtaining (D), according to claims 14 and 15.

In order to obtain a high degree of economy in the various preparation phases and thus also to secure the multi-stage processes according to the invention, it is particularly advantageous to employ a method according to claim 16 to prepare the starting materials for one of the "core zones" of the invention.

Claim 17 demonstrates a preferred route according to the invention for obtaining high yields of the particularly useful compounds (I), or (J).

A preferred method for the preparation of the compounds (I) and (J) from readily commercially available starting materials is described in claim 18.

If it is intended, within the framework of the invention, to produce a starting substance (K), which is referred to in claim 17—and this is a particularly preferred and also particularly advantageous substance both in terms of yield and purity—then preference should be given to the new and special synthesis route described in claim 19; it was found that special variants of individual stages of this synthesis, which are described in claims 20 and 21, are particularly advantageous both as regards yield and as regards the lack of disruptive side reactions.

Compounds (K) obtained in the course of the aforementioned advantageous reactions may be conveniently used to prepare compounds (I), as is provided for in claim 22.

In addition, in order to obtain high yields, special preference should be given to maintaining the process conditions, which have already been partially described, relating to solvents, reactands, acid binders (bases), catalysts and temperatures, as per one of the claims 23 and 24.

Special attention should also be drawn to the fact that all the processes, individual process steps and results described so far can be used with special advantage to prepare the furanoside derivatives having the above-mentioned formulae (DO) and (D1)), as described in claim 25.

The essential advantages of the invention and of the individual subjects of the invention may be described as follows: They make available a group of similar compounds or of intermediate compounds which permit, for the first time, chemically relatively uncomplicated and therefore economically very advantageous ways to be found for preparing the pharmaceutical active substances described at the beginning, which are rapidly gaining in importance for their high anti-viral effectiveness coupled with minimum cytotoxicity. The special advantages lie in particular in the fact that essentially only cheap or, if need be, cheaply prepared starting substances and reagents are required, the amount of apparatus and manipulation required is very modest, and each of the sections of the preparation processes or each of the preparation processes themselves, as claimed and as described in more detail above, is capable of providing surprisingly good yields of target products which are easy to separate from impurities.

Thus, compared with the state of the art, which so far was only able to provide processes requiring a large number—see the opening remarks—of extremely complicated stages, and only difficult-to-produce and expensive chemicals, and cumbersome reactions, it is now possible, and this is highly advantageous, for the first time to use multi-stage processes having economically very acceptable overall yield quotas in this field of furanoside derivatives. For the first time, a method has been shown which will help ensure that nothing now stands in the way of the wide-scale preparation and use of medications for controlling the diseases mentioned at the beginning.

It should furthermore be mentioned that, as has been shown, the arrangement of an ether protective group—which also comprises cyclic ether groups such as tetrahydropyranyl—in the 5 position of the new pentofuranoside derivatives, offers some very significant advantages for the preparation process, namely: The compounds and intermediates used and obtained according to the invention possess astonishingly high stability towards the reagents and process conditions used. Ultimately, this has a very advantageous effect on the separation, isolation and purification of each desired compound and thus, to a large extent, also on its yield.

Finally, it should not go unmentioned that the comprehensive use of the new compounds and intermediates prepared according to the invention, for the purposes set forth here in the description, and in particular in claims 26 and 27, together with the provisions contained therein, are essential aspects of the invention.

The present invention will now be described in more detail on the basis of the following examples, which describe typical compounds or intermediates and their preparation.

EXAMPLES

Example 1

To a suspension of 10 g of D-arabinose in 200 ml of dry methanol are added, drop by drop and while stirring, 50 ml of methanol containing 1 g of hydrogen chloride. After a reaction period of 7 hours, the reaction was neutralized with 2.8 g of triethylamine. The reaction solution was concentrated by evaporation under reduced pressure. The raw product obtained, namely methyl-D-arabinofuranoside, is dissolved without any further purification in 40 ml of dry pyridine and a catalytic amount of dimethyl aminopyridine is added. While stirring, 18.5 g of trityl chloride is added in portions. Stirring is continued at room temperature for 48 hours. Then, while cooling is carried out, 12 ml of methanesulfonyl chloride are added slowly, drop by drop. The reaction is allowed to continue at room temperature for 24 hours. The reaction solution is poured into 100 ml of iced water and extracted three times with 100 ml of methylene chloride each time. After the combined organic phases are dried, they are concentrated by evaporation under reduced pressure.

The mixture of anomers obtained in this manner is separated by column chromatography; 12.1 g of methyl-2,3-dimesyl-5-O-trityl-α-D-arabinofuranoside (34% yield) are obtained.

NMR (CDCL$_3$): 2.96(s,3H,OMs); 3.12(s,3H,OMs); 3.30 (dd, 1H,H-5 b, 3.6 Hz,10.5 Hz); 3.44(s,3H,OMe); 3.54(dd, 1H,H-5 a,3.8 Hz,10.5 Hz); 4.22(dt,1H,H-4,3.6 Hz,3.8 Hz,5.4 Hz); 5.09(dd,1H,H-2,0.6 Hz,1.6 Hz); 5.18(ddd,1H, H-3,0.7 Hz,1.6 Hz,5.4 Hz); 5.23(s,1H,H-1); 7.2–7.5 (m,15H,Tr)

Example 2

To 1 g of isopropyl-5-O-benzyl-α-D-arabinofuranoside, obtained by the method of Kawana et al. Bull.Chem-.Soc.Jpn. 54 (1981), 1492–1504, in 10 ml of pyridine, 0.6 ml of methanesulfonyl chloride are slowly added drop by drop while cooling with ice. The reaction is allowed to continue for 24 hours at room temperature. The reaction solution is poured into 20 ml of ice water and extracted three times with on each occasion 40 ml of methylene chloride. After the combined organic phases are dried, these are concentrated by evaporation under reduced pressure. The reaction mixture obtained in this manner is separated by column chromatography; 1.4 g of isopropyl-5-O-benzyl-2,3-dimesyl-α-D-arabinofuranoside are obtained (90% yield).

NMR (CDCL$_3$): 1.2(m,6H,2 CH3); 3,05(s,3H,OMs); 3.06 (s,3H,OMs); 3.74(dd,1H,H-5 b,4.0 Hz,10.9 Hz); 3.79(dd, 1H,H-5 a,4.0 Hz,10.9 Hz); 3.95(m,1H,CH(CH$_3$)$_2$); 4.31(dt, 1H,H-4,3.9 Hz,4.0 Hz,5.9 Hz); 4.61(2 d,2H,CH$_2$Ph,11.7 Hz); 5.2(dd,1H,H-2,0.9 Hz,2.1 Hz); 5.10(ddd,1H,H-3, 0.7 Hz,2.1 Hz,5.9 Hz); 5.32(s,1H,H-1); 7.4(m,5H,Ph)

Example 3

To a solution of 1.4 g of KOH and 0.5 g of NaBH$_4$ in 20 ml of isopropanol are added, in portions, at 60° C. and while stirring, 1 g of methyl-5-O-benzyl-2,3-dimesyl-α-D-arabinofuranoside, [IR(KBr) 1380, 1180 (S=0) 745,690 (benzyl)], prepared according to the manner described in Example 2. After the reaction has continued for 4 hours, it is quenched by using 4 ml of acetone, then neutralized with an acid ion exchanger, and the solution is concentrated by evaporation. The raw product obtained in this manner is separated by column chromatography; 0.35 g of methyl-5-O-benzyl-3-deoxy-α-D-erythropentofuranoside (60% yield) is obtained.

NMR (CDCL$_3$): 1.90(ddd,1H,H-3 b,7.4 Hz,8.4 Hz,12.6 Hz); 2.05(ddd, 1H,H-3 a,5.0 Hz,8.1 Hz,12.6 Hz); 3.43(dd, 1H,H-5 b,,5.2 Hz,10.3 Hz); 3.47 (s,3H,OMe); 3.51(dd,1H, H-5 a,3.6 Hz,10.3 Hz); 4.3(m,1H,H-2); 4.37 (m,1H,H-4); 4.57(s,2H,CH$_2$Ph); 4.88(d,1H,H-1,4.4 Hz) 7.35(m,5H,Ph)

Example 4

To a solution of 1.4 g of KOH and 0.5 g of NaBH$_4$ in 10 ml of methanol is added, drop by drop, at room temperature, while stirring, 1 g of methyl-2,3-dimesyl-5-O-trityl-α-D-xylofuranoside, obtained by the method of Feniou et al (EP 215.722), in 30 ml of methanol/MTBE 1/3. After the reaction has continued for 24 hours at room temperature, the mixture is diluted with 50 ml of MTBE and extracted three times with water, Then the organic phase is dried and concentrated by evaporation. The raw product obtained in this manner is separated by column chromatography; 0.38 g of methyl-3-deoxy-5-O-trityl-α-D-erythropentofuranoside (55% yield) is obtained.

NMR (CDCL$_3$): 1.90O(ddd,1H,H-3 b,7.3 Hz,8.3 Hz,12.6 Hz); 2.09(ddd, 1H,H-3 a,4.8 Hz,8.0 Hz,12.6 Hz); 3.03(dd, 1H,H-5 b,,4.4 Hz,9.9 Hz); 3.20(dd,1H,H-5 a,4.1 Hz,9.9 Hz); 3.50 (s,3H,OMe); 4.3–4.4(m,2H, H-2,H-4); 4.94(d,1H,H-1, 4.4 Hz); 7.2–7.5(m,15H,Tr)

Example 5

To 0.35 g of DAST, dissolved in 5 ml of methylene chloride, are added 0.5 ml of pyridine and cooling is then carried out to 2° C. under N$_2$. Then, 0.78 g of methyl-3-deoxy-5-O-trityl-α-D-erythropentofuranoside, obtained from Example 4, are slowly added; the reaction is allowed to continue for 3 hours at room temperature. The reaction is stopped by adding 10 ml of methanol at room temperature and, after 1 hour, concentration by evaporation is carried out under reduced pressure. The raw product obtained in this manner is separated by column chromatography; 0.53 g of methyl 2,3-dideoxy-2-fluoro-5-O-trityl-α-D-threopentofuranoside (68% yield) are obtained.

NMR (CDCL$_3$): 1.92(ddddd,1H,H-3 b,0.8 Hz,1.3 Hz,5.0 Hz,$^{14.6}$ Hz, 31.0 Hz); 2.32 (dddd,1H,H-3 a,5.9 Hz,8.4 Hz,$^{14.6}$ Hz,35.4 Hz); 3.13 (dd,1H,H-5 b,5.2 Hz, 9.6 Hz); 3.30(dd,1H,H-5 a,0.5 Hz,5.9 Hz,9.6 Hz); 3.70(s,3H,OMe); 4.32(m,1H,H-4); 4.92 (ddd,1H,H-2,1.2 Hz,5.6 Hz, 53.0 Hz); 5.08(d,1H, H-1,9.8 Hz); 7.1–7.5 (m,15H,Tr)

Example 6

To a solution of 0.40 g of methyl-5-O-benzyl-3-deoxy-α-D-erythropentofuranoside, obtained according to Example 3, and 0.4 ml of pyridine in 4 ml of methylene chloride are added, drop by drop, at −30° C., while stirring, 0.33 ml of trifluoromethanesulfonyl anhydride in 10 ml of methylene chloride. Cooling to 0° C. is carried out over a period of 3 hours; the organic phase is washed with ice cold water, cold 5% H$_2$SO$_4$, and saturated NaHCO$_3$; drying is carried out over MgSO$_4$; and at −25° C. a solution of 3.7 g of tetrabutylammonium fluoride-trihydrate in 10 ml of methylene chloride is added drop by drop. The mixture is allowed to return slowly to room temperature and the reaction continues for another 24 hours. Then the organic phase is washed with water, dried over MgSO$_4$ and concentrated by evaporation. The raw product obtained in this manner is separated by column chromatography; 0.14 g of methyl-5-O-benzyl-2,3-dideoxy-2-fluoro-α-D-threopentofuranoside (35% yield) are obtained.

NMR (CDCL$_3$): 1.86(ddddd,1H,H-3 b,0.8 Hz,1.0 Hz,4.6 Hz,14.7 Hz, 30.2 Hz); 2.36 (dddd,1H,H-3 a,5.4 Hz,8.7 Hz,14.7 Hz,37.5 Hz); 3.36 (s,3H,OMe); 3.50(dd,1H,H-5 b,4.8 Hz, 10.0 Hz); 3.60(ddd,1H,H-5 a, 0.6 Hz,6.9 Hz,10.0 Hz); 4.37(m,1H,H-4); 4.61(2d,2H,CH$_2$Ph,12.2 Hz); 4.95 (ddd,1H,H-2,1.1 Hz,5.3 Hz,52.9 Hz); 5.10(d,1H,H-1,9.6 Hz); 7.36 (m,5H,Ph)

Example 7

To a solution of 0.5 g of NaOH in 3 ml of H$_2$O are added, in portions, at 20° C., while stirring; 0.5 g of methyl-2,3-ditosyl-5-O-trityl-α-D-xylofuranoside [IR(KBr 1600 (tosyl) 705 (phenyl)], prepared in the manner described in Example 1, in 10 ml of dioxan. After the reaction has continued for 24 hours it is neutralized with CO$_2$, filtration is carried out and the solution is concentrated by evaporation. The raw product thus obtained is separated by column chromatography; 0.13 g of methyl-3-deoxy-5-O-trityl-α-D-glycopentofuranoside-2-ulose (48% yield) are obtained.

(IR(KBr) 1773 (C=O) 705 (phenyl)

Example 8

To a solution of 0.5 g of methyl-5-O-benzyl-2,3-dimesyl-α-D-arabinofuranoside, obtained according to the method described in Example 2, in 10 ml of dry MTBE, is added 0.1 g of sodium methylate at room temperature. After the reaction has continued for 24 hours it is neutralized with $CO_2$, filtration is carried out and the solution is concentrated by evaporation. The raw product obtained in this manner is separated by column chromatography and 0.11 g of methyl-5-O-benzyl-3-deoxy-2-O-mesyl-α-D-glyceropent-2-enofuranoside (29% yield) are obtained.

IR(KBr) 1670 (C=C—OMs) 1380, 1180 (S=O) 745,690 (benzyl)

Example 9

To a solution of 1 g of isopropyl-5-O-benzyl-3-deoxy-α-D-threopentofuranoside, obtained according to the manner described in Examples 2 and 3, and 2 g of imidazole in 50 ml of dry ethyl acetate, are slowly added, drop by drop, 0.45 ml of sulfuryl chloride in 5 ml of ethyl acetate, at −30° C. The reaction is allowed to continue for 12 hours at room temperature; the organic phase is washed with 5% $H_2SO_4$, $NaHCO_3$ solution; drying is carried out over $MgSO_4$ and the solution is concentrated by evaporation under reduced pressure. The residue and 1 g of KHF2 are suspended in ethylene glycol and heated at 110° C. for 1 hour in the presence of 0.2 ml of 50% HF. The reaction mixture is poured into 20 ml of $H_2O$, dried over $MgSO_4$ and then concentrated by evaporation. The raw product obtained in this manner is separated by column chromatography; 0.35 g of isopropyl-5-O-benzyl-2,3-dideoxy-2-fluoro-α-D-threopentofuranoside (35% yield) are obtained.

Example 10

350 mg of $I_2$ were added to a stirred suspension of 5 g of D-xylose in 250 ml of dry methanol. After stirring for six hours, with reflux, exclusively furanosides were formed. Next, the reaction solution was cooled, treated with 430 mg of $Na_2S_2O_3$ and concentrated by evaporation under reduced pressure. The yield of raw product was 6.30 g of an anomeric mixture of methyl-D-xylofuranosides (100%). Since the raw product formed is already suitably pure for the next reaction stage, it was used in that stage without further purification.

Example 11

The residue from Example 10 is diluted with 3 ml of DMF and 29.1 g of benzaldehyde dimethyl acetal are added. While stirring, 90 mg of p-toluenesulfonic acid are added. The reaction is terminated after 30 min. at room temperature and it is neutralized by triethyl amine. The solution is concentrated by evaporation at reduced pressure, taken up in 250 ml of $CH_2Cl_2$, shaken once with 50 ml of a 1% $Na_2SO_4$ solution, and three times with 100 ml of water, dried with $MgSO_4$ and evaporated to dryness at reduced pressure. The raw product obtained in this way is separated by column chromatography; 3.44 g of methyl-3,5-O-benzylidene-α-D-xylofuranoside (41% yield) are obtained; mp 80–85° C., RF ($CH_2Cl_2$/acetone 85/15): 0.59.

Example 12

To a solution of 1.00 g of methyl-3,5-O-benzylidene-α-D-xylofuranoside obtained from Example 11, and 1.70 g of $NaCNBH_3$ in 30 ml of THF abs., 8 ml of a cold, HCl-saturated solution of diethyl ether are added drop by drop, while stirring, in such a way that no gas is seen to be generated. After 1 hour, the reaction is completed. The solution is diluted with 100 ml $CH_2Cl_2$ and then extracted with water, $NaHCO_a$ solution, water, dried with $MgSO_4$ and concentrated by evaporation at 30° C. at reduced pressure. The raw product obtained in this manner is separated by column chromatography; 0.84 g of methyl-5-O-benzyl-α-D-xylofuranoside (84% yield). $[\alpha]_0$=+94.1 (c=1.45, $CH_2Cl_3$),RF 0.40 ($CH_2Cl_2$/MeOH 96/4).

Example 13

A solution of 300 mg of methyl-2,3-dideoxy-2-fluoro-5-O-(p-chlorotrityl)-α-D-threopentofuranoside, obtained in a manner similar to that used in Example 5, was treated at room temperature with a 30% Hbr/HOAc solution. After 1 hour the reaction solution was concentrated by evaporation under vacuum and the residue was taken up in 1 ml of acetonitrile.

To this solution was added freshly prepared silylated 6-chloropurine in 3 ml of acetone, and stirred at 70° C. for 24 hours. The solution was evaporated to dryness under vacuum. The raw product obtained in this manner was separated by column chromatography; 35 mg of 6-chloro-9-[2,3-dideoxy-2-fluoro-5-O-(p-chlorotrityl)-β-D-threopentofuranosyl]-9-H-purine (9% yield) was obtained.

| NMR($CDCL_3$): | 2.3–2.6(m; 2H; H-3'a; H3'b); | 3.2–3.4(m; 2H; H-5–a; H5–b); | 4.4(m; 1H; H-4'); |
|---|---|---|---|
| | 5.3(dm; 1H; H-2'; 53 Hz); | 6.4(dd; 1H; H-1'; 2.7 Hz; 19.7 Hz); | |
| | 7.1–7.6(m; 14H; p-Cl—Tr); | 8.4(d; 1H; H-8; 2.6); | 8.7(s; 1H; H-2) |

Example 14

A solution of 200 mg of methyl-5-O-(p-methoxy-benzyl)-2,3-dideoxy-2-fluoro-α-D-threopentofuranoside in 20 ml of acetyl bromide was stirred at room temperature overnight. The reaction solution was evaporated to dryness under vacuum and taken up in $CH_2Cl_2$. To this solution was added, at 60° C., while stirring, a solution of the sodium salt of adenine in acetonitrile. After 5 hours, the solution was filtered, evaporated to dryness, taken up in MTBE, washed, dried with $MgSO_4$, evaporated under reduced pressure and dried. The raw product obtained in this way was separated by column chromatography; a total of 43 mg of 9-(5-O-(p-methoxy-benzyl)-2,3-dideoxy-2-fluoro-β-D-threopentofuranosyl]-adenine (15% yield) was obtained.

| | | |
|---|---|---|
| NMR(CDCL₃): | 2.3–2.6(m; 2H; H-3'a; H3'b); | 3.5–3.7(m; 2H; H-5'a; H5'b); |
| 3.8(s; 1H; OMe); | 4.5(m; 1H; H-4'); | 4.6(2d; 2H; CH2Ph); |
| 5.4(dm; 1H; H-2'; 53 Hz); | 6.4(dd; 1H; H-1'; 2.7 Hz; 19.7 Hz); | 6.8–7.2(m; 4H; Ph); |
| 7.3(br s; 2H; NH₂) | 8.4(d; 1H; H-8; 2.6); | 8.7(s; 1H; H-2) |

Example 15

370 mg of 9-[5-O-(p-methoxy-benzyl)-2,3-dideoxy-2-fluoro-β-D-threopentofuranosyl]-adenine, obtained from Example 14, in 150 ml of ethanol are stirred in a hydrogenation apparatus at room temperature, under hydrogen, in the presence of 0.5 g of 10% Pd/C catalyst and 0.5 ml of acetic acid until the volume of the absorbed hydrogen remains constant. Then the apparatus is flushed with argon. The catalyst is removed by filtration and washed twice with ethanol, and the combined organic phases are evaporated to dryness at reduced pressure. The raw product obtained is separated by column chromatography; a total of 193 mg of 9-[2,3-dideoxy-2-fluoro-β-D-threopentofuranosyl]-adenine (68% yield) was obtained.

Fp. 227° C. NMR identical to that given in the literature.

The following diagram 3 shows the reaction sequence of the invention according to claims 19, 20, 21 or the Examples 10 to 12, and in the diagram the substituents $R^*$, $R_0$ and $R_1^2$, have the meanings already mentioned above.

Diagram 3:

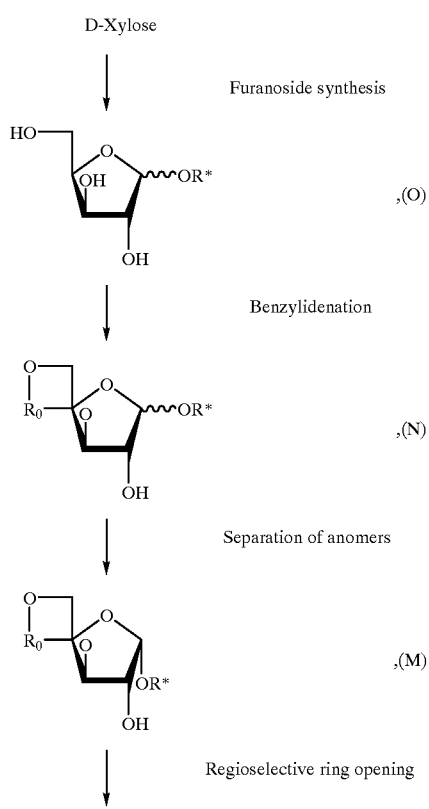

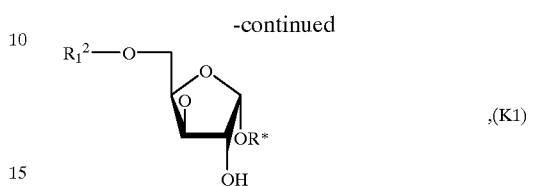

We claim:

1. An α-D-pentofuranoside derivative having the general formula (F)

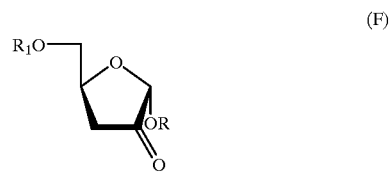

wherein R is a $(C_1-C_4)$alkyl that is non-substituted or substituted one or more times by halogen, $(C_1-C_4)$alkyl, $(C_1-C_4)$alkoxy and/or phenyl; and $R_1$ is a $\{(C_6-C_{20})\text{aryl}\}_k-\{(C_1-C_4)\text{alkyl}\}$(k=0 to 3) or $(C_6-C_{20})$aryl, that is non-substituted or substituted one or more times by halogen, $(C_1-C_4)$alkyl, $(C_1-C_4)$alkoxy and/or $(C_6-C_{20})$aryl.

2. The derivative according to claim 1 wherein $R_1$ is a benzyl that is non-substituted or substituted one or more times by halogen, $(C_1-C_4)$alkyl, $(C_1-C_4)$alkoxy and/or $(C_6-C_{20})$aryl.

3. An α-D-pentofuranoside derivative having the general formula (H)

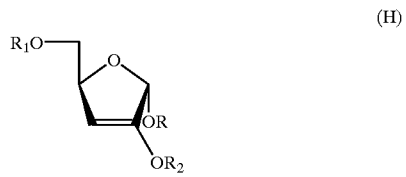

wherein R is a $(C_1-C_4)$alkyl that is non-substituted or substituted one or more times by halogen, $(C_1-C_4)$alkyl, $(C_1-C_4)$alkoxy and/or phenyl; $R_1$ is a $\{(C_6-C_{20})\text{aryl}\}_k-\{(C_1-C_4)\text{alkyl}\}$(k=0 to 3), $(C_1-C_{20})$aryl or $\{(C_6-C_{20})\text{aryl}\}_k-(C_c-C_{12})\text{alkyl}\}_{(3-k)}$Si(k=0 to 3), that is non-substituted or substituted one or more times by halogen, $(C_1-C_4)$alkyl, $(C_1-C_4)$alkoxy and/or $(C_6-C_{20})$aryl; and $R_2$ is an alkyl or aryl, sulfonyl or acyl group that is non-substituted or substituted one or more times by halogen, $(C_1-C_4)$alkyl, $(C_1-C_4)$alkoxy and/or phenyl.

4. The derivative according to claim 3 wherein $R_2$ is a methanesulfonyl group or a toluenesulfonyl group that is non-substituted or substituted one or more times by halogen, $(C_1-C_4)$alkyl, $(C_1-C_4)$alkoxy and/or phenyl.

5. An α-D-pentofuranoside derivative having the general formula (I) or (J)

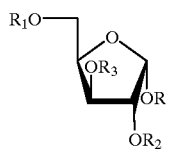

(I)

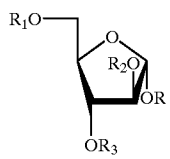

(J)

or mixtures of the derivatives (I) and (J), wherein R is a $(C_1-C_4)$alkyl that is non-substituted or substituted one or more times by halogen, $(C_1-C_4)$alkyl, $(C_1-C_4)$alkoxy and/or phenyl; $R_1$ is a $\{(C_6-C_{20})aryl\}_k-\{(C_1-C_4)alkyl\}$(k=0 to 3), $(C_6-C_{20})$aryl or $\{(C_6-C_{20})aryl\}_k-(C_1-C_{12})alkyl\}_{(3-k)}$Si(k=0 to 3), that is non-substituted or substituted one or more times by halogen, $(C_1-C_4)$alkyl, $(C_1-C_4)$alkoxy and/or $(C_6-C_{20})$aryl; and $R_2$ and $R_3$, which may be the same or different, are an alkyl or an aryl, or a sulfonyl group that is non-substituted or substituted one or more times by halogen, $(C_1-C_4)$alkyl, $(C_1-C_4)$alkoxy and/or phenyl; with the proviso that, for compound (I), R cannot be methyl or ethyl when $R_1$ is trityl and $R_2$ and $R_3$ are each a methanesulfonyl group.

6. The derivative according to claim 5 wherein $R_2$ and $R_3$ are a methanesulfonyl group or a toluenesulfonyl group that is non-substituted or substituted one or more times by halogen, $(C_1-C_4)$alkyl, $(C_1-C_4)$alkoxy and/or phenyl.

7. A process for preparing α-D-pentofuranoside derivatives having the general formula (D)

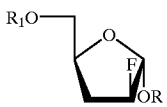

(D)

wherein R is a $(C_1-C_4)$alkyl that is non-substituted or substituted one or more times by halogen, $(C_1-C_4)$alkyl, $(C_1-C_4)$alkoxy and/or phenyl; and $R_1$ is a $\{(C_6-C_{20})aryl\}_k-\{C_1-C_4)alkyl\}$(k=0 to 3), $(C_6-C_{20})$aryl or $\{(C_6-C_2)aryl\}_k-(C_1-C_{12})alkyl\}_{(3-k)}$Si(k=0 to 3), that is non-substituted or substituted one or more times by halogen, $(C_1-C_4)$alkyl, $(C_1-C_4)$alkoxy and/or $(C_6-C_{20})$aryl; said process comprising:

(a) introducing a nucleofuge leaving group into a compound having the general formula (E)

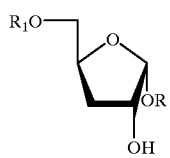

(E)

wherein R and $R_1$ are as defined for compound (D);
(b) replacing the nucleofuge leaving group with fluoride; and
(c) obtaining compound (D).

8. The process according to claim 7 wherein said replacement step (b) takes place in the presence of an acid and a source of fluoride ion.

9. The process according to claim 7 wherein $R_1$ of compound (D)

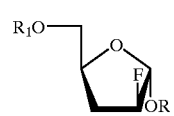

(D)

is a benzyl that is non-substituted or substituted one or more times by halogen, $(C_1-C_4)$alkyl, $(C_1-C_4)$alkoxy and/or $(C_6-C_{20})$aryl.

10. The process according to claim 7, wherein the conversion of compound (E)

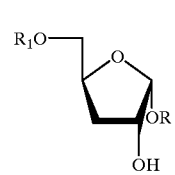

(E)

to compound (D)

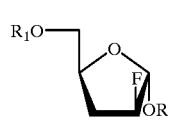

(D)

is carried out in at least one of the solvents selected from the group of polar aprotic solvents consisting of a chlorinated hydrocarbon, an ether, a carboxylic acid ester, a nitrile or an alcohol.

11. The process according to claim 7 wherein the conversion of compound (E)

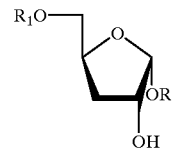

(E)

to compound (D)

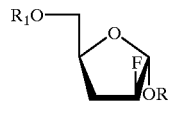

(D)

is carried out in at least one solvent selected from the group consisting of methylene chloride, tetrahydrofuran, acetonitrile, butanol and ethylene glycol.

12. The process according to claim 7 wherein the nucleofuge leaving group is selected from the group consisting of a trifluoromethanesulfonyl, a p-bromobenzenesulfonyl and an imidazolesulfonyl group.

13. The process of claim 7 wherein said replacement step (b) takes place under the influence of a source of a fluoride ion which is one or more compounds selected from the group consisting of an alkali ammonium fluoride, an alkaline earth ammonium fluoride, atri($C_1$–$C_4$) alkyl ammonium fluoride, a tetra($C_1$–$C_4$)alkyl ammonium fluoride, pyridinium fluoride and polyhydrogen fluoride.

14. The process of claim 7 wherein the fluoride is from tetrabutylammonium fluoride.

15. The process according to claim 7 wherein the temperature of the replacement reaction in step (b) is maintained in a range from 10 to 150° C.

16. The process according to claim 8 wherein the conversion of the compound (E)

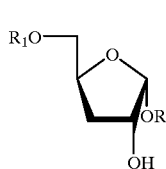

(E)

to (D)

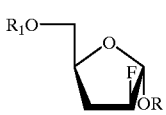

(D)

is carried out in at least one of the solvents selected from the group consisting of polar, aprotic solvents, chlorinated hydrocarbons, alcohols, ethers, polyols, carboxylic acid esters, nitrites, methylene chloride, tetrahydrofuran, acetonitrile, butanol and ethylene glycol; wherein the source of fluoride ion is one or more compounds selected from the group consisting of an alkali ammonium fluoride, an alkaline earth ammonium fluoride, a tri($C_1$–$C_8$) alkyl ammonium fluoride, a tetra($C_1$–$C_8$)alkyl ammonium fluoride, tetrabutylammonium fluoride, pyridinium fluoride and polyhydrogen fluoride; wherein the nucleofuge leaving group is selected from the group consisting of a trifluoromethanesulfonyl group, a p-bromobenzenesulfonyl group and a imidazolesulfonyl group; and wherein the temperature of the replacement reaction in step (b) is maintained between 10 to 150° C.

17. A process for preparing α-D-pentofuranoside derivatives having the general formula (D)

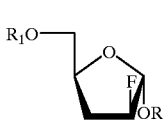

(D)

wherein R is a ($C_1$–$C_4$)alkyl that is non-substituted or substituted one or more times by halogen, ($C_1$–$C_4$)alkyl, ($C_1$–$C_4$)alkoxy and/or phenyl; and $R_1$ is a $\{(C_6$–$C_{20})aryl\}_k$–$\{C_1$–$C_4)alkyl\}(k=0$ to $3)$, ($C_6$–$C_{20}$)aryl or $\{(C_1$–$C_{20})aryl\}_k$–$(C_1$–$C_{12})alkyl\}_{(3-k)}Si(k=0$ to $3)$, that is non-substituted or substituted one or more times by halogen, ($C_1$–$C_4$)alkyl, ($C_1$–$C_4$)alkoxy and/or ($C_6$–$C_{20}$)aryl; said process comprising:

(a) reacting a compound having the general formula (E),

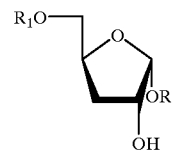

(E)

wherein R and $R_1$ are as defined for compound (D), with diethylaminosulfur trifluoride (DAST); and (b) obtaining compound (D)

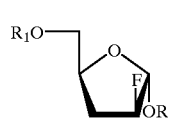

(D)

from the reaction mixture generated by step (a).

18. The process according to claim 17 wherein $R_1$ of compound

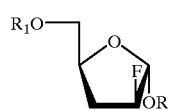

(D)

is a benzyl that is non-substituted or substituted one or more times by halogen, ($C_1$–$C_4$)alkyl, ($C_1$–$C_4$)alkoxy and/or ($C_6$–$C_{20}$)aryl.

19. The process according to claim 17, wherein the conversion of compound (E)

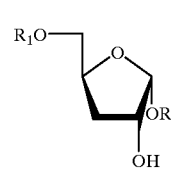

(E)

to compound (D)

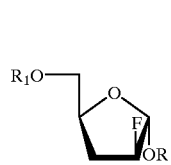

(D)

is carried out in at least one of the solvents selected from the group of polar aprotic solvents consisting of a chlorinated hydrocarbon, an ether, a carboxylic acid ester, a nitrile and an alcohol.

20. The process according to claim 17 wherein the conversion of compound (E)
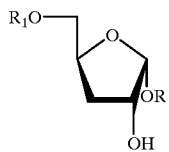
(E)
to compound (D)
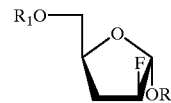
(D)
is carried out in at least one solvent selected from the group consisting of methylene chloride, tetrahydrofuran, acetonitrile, butanol and ethylene glycol.
* * * * *